United States Patent [19]
Epstein et al.

[11] Patent Number: 6,007,515
[45] Date of Patent: Dec. 28, 1999

[54] CONTROLLED ACTION, MANUALLY OPERABLE FLUID APPLICATION

[76] Inventors: Gordon Howard Epstein, 135 Kootenai Dr., Fremont, Calif. 94539; Alan Kirby Plyley, 160 N. Fairview #D183; Russell James Redmond, 1148 N. Fairview, both of Goleta, Calif. 93117

[21] Appl. No.: 08/946,364

[22] Filed: Oct. 7, 1997

Related U.S. Application Data

[63] Continuation-in-part of application No. 08/838,078, Apr. 15, 1997.

[51] Int. Cl.$^6$ .................................................. A61M 37/00
[52] U.S. Cl. ............................. 604/82; 604/73; 604/131; 604/181; 604/191; 604/208; 604/218; 604/224; 604/228
[58] Field of Search ................................. 604/82, 73, 94, 604/131, 135, 134, 173, 181, 187, 191, 208, 214, 218, 224, 228, 46, 49, 56; 222/137, 327, 391; 424/423

[56] References Cited

U.S. PATENT DOCUMENTS

| | | |
|---|---|---|
| 4,040,420 | 8/1977 | Speer . |
| 4,359,049 | 11/1982 | Redl et al. . |
| 4,516,442 | 5/1985 | Davis . |
| 4,735,616 | 4/1988 | Eibl et al. . |
| 4,874,368 | 10/1989 | Miller et al. . |
| 4,978,336 | 12/1990 | Capozzi et al. . |
| 5,061,180 | 10/1991 | Wiele . |
| 5,116,315 | 5/1992 | Capozzi et al. . |
| 5,226,877 | 7/1993 | Epstein . |
| 5,328,459 | 7/1994 | Laghi . |
| 5,395,326 | 3/1995 | Haber et al. ............................... 604/90 |
| 5,405,607 | 4/1995 | Epstein . |
| 5,520,658 | 5/1996 | Holm ....................................... 604/191 |
| 5,584,815 | 12/1996 | Pawelka et al. .......................... 604/191 |
| 5,612,050 | 3/1997 | Rowe et al. ............................. 424/423 |
| 5,749,968 | 5/1998 | Melanson et al. ....................... 118/300 |
| 5,759,171 | 6/1998 | Coelho ...................................... 604/82 |

*Primary Examiner*—Corrine McDermott
*Assistant Examiner*—Kent Gring
*Attorney, Agent, or Firm*—Handal & Morofsky

[57] ABSTRACT

The invention provides a handheld, manually operable fluid applicator, particularly suited to the needs of surgeons, which can dispense multiple medically useful fluids, for example fibrin and thrombin components of a tissue adhesive, and which has a smooth feel and action. The applicator has a novel actuator mechanism providing a comparatively higher mechanical advantage in a commencement phase of the actuator stroke and a comparatively lower mechanical advantage in a completion phase of the actuator stroke.

19 Claims, 11 Drawing Sheets

CONTROLLED ACTION, MANUALLY OPERABLE FLUID APPLICATION

CROSS-REFERENCE TO A RELATED APPLICATION

This application is a continuation-in-part of copending U.S. patent application Ser. No. 08/838,078 of Gordon Howard EPSTEIN et al. filed Apr. 15, 1997 now pending and entitled "APPLICATOR FOR DISPENSING MEASURED QUANTITIES WITH USE OF CONTROLLED SUCTION", (referenced as the "parent", or "parent application" herein) the disclosure of which is hereby incorporated herein by reference thereto.

BACKGROUND OF THE INVENTION

1. Field of the Invention

This invention relates to a controlled action, manually operable fluid applicator of the type in which a user, while holding the applicator in one hand, operates a fluid dispensing actuator to drive fluid from a reservoir and out of the applicator, through an applicator tip. Such applicators have many different uses and are particularly well suited for dispensing glues and adhesives and indeed are common household items for applying epoxy glues, viscous carpentry glues and caulks and so on. More specialized uses with greater performance requirements, as will be described herein, are for applying tissue adhesives in a surgical context to repair tissues damage, and for equivalent professional, medical, veterinary or biological uses.

2. Description of Related Art Including Information Disclosed under 37 CFR 1.97 and 37 CFR 1.98

The above described fluid applicators provide better control over the fluid emerging from the applicator than is possible by simply squeezing a deformable tube of glue to expel the glue from a nozzle attached to the tube. Nevertheless, the control achievable with known applicators is insufficiently precise for many applications. In particular, in surgical applications, there is a need for a fluid dispenser to dispense tissue adhesive which can be precisely and predictably controlled by the user to dispense and apply small quantities of adhesive to target locations. Furthermore, there is a need for an applicator that can be held in a number of different ergonomically desirable configurations. There are a number of teachings in the literature of specialized applicator constructions including those of the present inventor, which have been designed to meet the particular needs of tissue adhesive application, but none is wholly satisfactory owing to deficiencies in the drive mechanism which translates manual force applied to the actuator into movement of the fluid out of the applicator.

In an important optional construction, multiple fluids are held in multiple reservoirs may be dispensed with or without mixing within the applicator. Common household epoxy glue applicators dispense parallel streams of resin and hardener for external mixing and teach that mixing within the applicator, or on its external surfaces, should be avoided to prevent bonding and blockage of its fluid passageways. In contrast, a tissue adhesive applicator, such for example as disclosed in Epstein U.S. Pat. Nos. 5,226,877 and 5,405,607 has reservoirs for two fluids, for example a fibrinogen-containing phase and a thrombin-containing phase, a mixing chamber and a single outlet port for the mixed fluids.

In the described applicators, manual effort provides the necessary drive force and typically, but not necessarily, the applicator has a barrel which can be comfortably held while leaving the thumb free to operate the dispensing actuator which is conveniently positioned for the purpose. An extended applicator tip, which may have a variety of conformations, enables skilled users to apply the dispensed fluid to a target location with considerable precision. Preferably, the applicator is neutral to handedness, being equally amenable to left-hand or right-hand operation. A well known fluid applicator construction comprises a barrel-like body intended to be gripped in the user's hand, which body incorporates a fluid reservoir, and a trigger-like, spring-return fluid-dispensing actuator, manually applied pressure on which drives fluid out of the reservoir through an applicator tip. The drive mechanism comprises a toothed rack extending the length of the reservoir to be discharged, a plunger and a drive pawl, the plunger and drive pawl being coupled with the trigger actuator via pivot means so that operation of the actuator causes the drive pawl to engage the rack teeth, to pivot and index the plunger into the reservoir. On the return path, the drive pawl rides back over the rack while engagement of a second, locking pawl with the toothed rack prevents drawback. Such applicators are commonly available in hardware stores and are standard issue for dispensing and applying caulking, construction adhesive and the like. Generally, they provide an increasing mechanical advantage as the trigger is squeezed, making steady controlled application of fluid difficult to achieve. For this and other reasons, such hardware store applicators are not suited to medical and surgical uses.

Laghi, U.S. Pat. No. 5,328,459, addresses the need for generating high pressures to produce low flow rates when dispensing thixotropic or non-Newtonian fluids. Laghi employs small electric motors, preferably stepper motors, for providing high torque when driving a dispenser which expensive and cumbersome remedy does not solve the problems faced by surgeons wishing to apply one or more medically useful fluids to patients during surgery.

Rowe et al., U.S. Pat. No. 5,612,050, discloses an applicator which employs a trigger-actuated compression spring to provide a driving force for dispensing polymeric fluids to a site on the tissue of a patient. The trigger 182 includes a cam surface 180 which increases the mechanical advantage on a compression link 158 as the squeezing of the trigger progresses providing the user with an unbalanced response, making it difficult adequately to control the discharge of fluid.

There is accordingly a need for a manually operable fluid applicator that has a controlled action suiting it to precision applications such, for example, as dispensing and applying medically useful fluids during surgery.

SUMMARY OF THE INVENTION

The invention, as claimed, is intended to provide a remedy. It solves the problem of providing a manually operable fluid applicator with a precisely controllable action for dispensing small quantities of fluids. Accordingly, the invention provides a manually actuated fluid applicator having:

a) a fluid container to contain fluid;

b) a movable actuator repeatedly operable, with an actuator stroke effected by a manually applied force on the movable actuator, to dispense fluid from the applicator by displacement of fluid from the fluid container, the actuator stroke having a commencement phase and a completion phase; and c) a drive mechanism to translate the manually applied force on the movable actuator to a fluid displacing force exerted on fluid in the fluid container;

wherein the mechanical advantage of the drive mechanism with regard to the ratio of the fluid-displacing force to the manually applied force is proportionately larger in the commencement phase and smaller throughout the completion phase.

By providing a relatively higher mechanical advantage in the commencement phase of the actuator stroke initial frictional resistance and inertia can readily be overcome while a smaller mechanical advantage during the completion phase enables the user precisely to control the quantity of fluid dispensed and to avoid inadvertent excesses.

Preferably, the mechanical relationships in the commencement and the completion phases respectively are such as to overcome initial frictional resistance and provide a smooth feel of the actuator throughout the stroke.

In a preferred embodiment, the actuator can comprise a manually engageable and depressible actuator member, a driving member and a pivoted link having one end pivoted to the driving member and having another end, the applicator further comprising a driving connection between the depressible actuator member and the other end of the pivoted link the driving connection providing freedom of movement of the other end of the pivoted link in a direction to reduce the proportion of drive force transmitted as the stroke advances.

Also in a preferred embodiment, the applicator is a plural fluid applicator having a plurality of fluid containers respectively for a plurality of fluids and wherein the drive mechanism acts on fluids in the fluid containers in harness to exert a fluid displacing force on each fluid simultaneously.

BRIEF DESCRIPTION OF THE DRAWINGS

Some illustrative embodiments of the invention, and the best mode contemplated of carrying out the invention, are described in detail below with reference to the accompanying drawings in which.

DETAILED DESCRIPTION OF THE PREFERRED EMBODIMENTS

Figure 1:
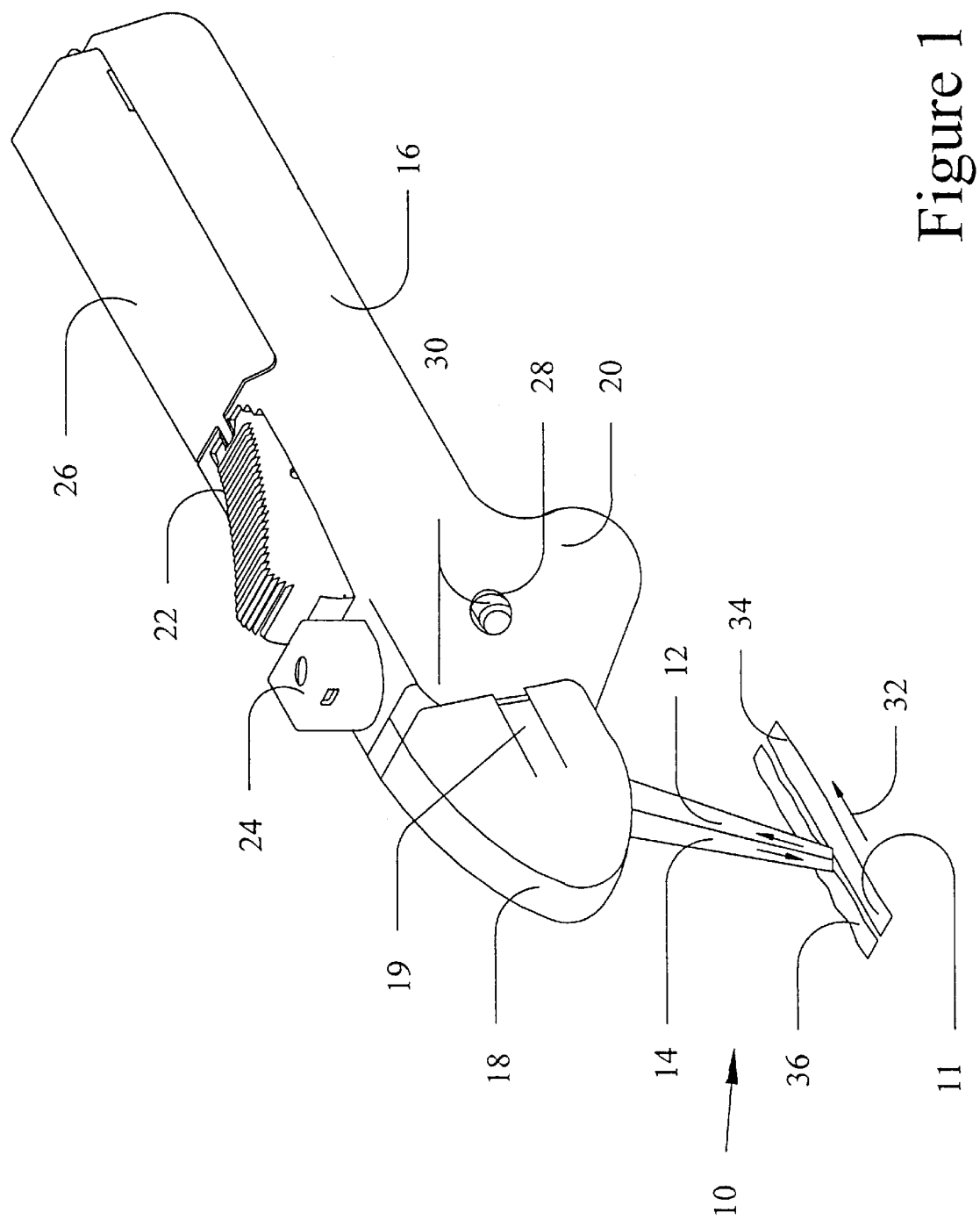
FIG. 1 is a perspective view of one embodiment of medical fluid applicator employing an actuating mechanism according to the invention.

FIG. 1 gives a good overall impression of the exterior, three-dimensional configuration of a preferred embodiment of medical fluid applicator, incorporating the invention, which applicator is particularly suited to the application of tissue adhesive during human or veterinary surgery.

Referring to FIG. 1, the medical fluid applicator shown is a handheld device which has an applicator tip 10 intended to be drawn across a tissue surface 11 to discharge one or more fluids under the control of an operator, who may well be a surgeon or physician. The applicator tip 10 comprises an aspiration tube 12, coupled to a vacuum source (not shown), and a fluid dispensing tube 14, which communicates with one or more medical fluid sources within the applicator.

While the term "fluid" as used in physics may comprise any matter in the liquid or gaseous state, the applicators described herein, aside from their described aspirator functions are not specifically intended for dispensing gases. Accordingly the use of the term "fluid" herein is intended to embrace flowable, non-gaseous materials that can usefully be dispensed from the described applicators, including liquids, dispersions, gels slurries and the like, being suspensions of solid particles in a liquid phase, thixotropic and semi-solid materials. Those skilled in the art will understand that more viscous fluid may require relatively large passageways and ports, while less viscous fluids may require better seals to prevent leakage.

The purpose of FIG. 1 is to suggest one possible general external appearance of a preferred embodiments of applicator according to the invention, and its use. The more detailed embodiment shown in FIGS. 2–5 has small differences in external appearance from the FIG. 1 embodiment, which differences can be seen when the drawings are read carefully along with the description herein. As will be described in more detail hereinbelow, preferred embodiments of the applicator shown are suitable, inter alia, for surgical or even microsurgical applications, where pinpoint control of every procedural step is essential, and enable a surgeon or other user to dispense and apply one or more medically useful fluids from applicator tip 10 to tissue surfaces, in an esthetic, precisely controllable process which can be augmented by the controlled application of suction. The particular embodiment illustrated also provides for premixing of two fluids contained in separate reservoirs prior to discharge through dispensing tube 14 and for applying suction to clear reaction product debris from dispensing tube 14. Other embodiments could dispense a single fluid without premixing, premix three or more fluids, or dispense multiple fluids from multiple reservoirs, without premixing, if desired, as will be apparent to those skilled in the art in light of this disclosure.

The applicator has a longitudinally extending, barrel-like body housing 16 terminating in a forward tip housing 18 from which applicator tip 10 depends downwardly. The applicator can be comfortably received into a user's hand, either into the palm, or between the thumb, fore- and index fingers, like an oversized pen, where it will usually be held with tip housing 18 projecting outwardly in front of the user, as an extension of the user's hand. Directions such as "forward" and "rearward", are used herein in this sense of being, respectively, remote from, or near to, a point of origin or attachment, tip housing 18 being forward while body housing 16 is rearward. Other directions assume, merely for reference purposes, that the user holds the applicator with body housing 16 extending approximately horizontally. Resiliently depressible latches 19 enable tip housing 18 to be removed to permit recharging of the applicator with fluids and to permit attachment of a different tip housing 18 providing different functionality, for example as described in parent application Ser. No. 08/838,078.

Just behind tip housing 18, a tubular housing extension also depends downwardly to provide a suction port 20 which contains within it a suction connector (to be described). Suction port 20 also serves as a guard or guide for the user's digits, positioning them, in the case of surgical users, clear of patient tissues or fluids, and of any surgical instruments in the vicinity of the work area.

Projecting upwardly from body housing 16 is a button-like fluid dispensing actuator, or trigger 22, conveniently positioned for operation by a user's thumb. Just forwardly, or distally, of the trigger 22, a depressible control valve button 24, which also projects upwardly from body housing 16, operates a valve (to be described), within body housing 16, to control the application of suction. Both trigger 22 and control valve button 24 are spring biased to the raised positions shown.

A hinged cover 26 overlies a major portion of the rearward end of the applicator, providing access to the interior for reloading, maintenance and disassembly, while forwardly located viewing ports 28, positioned on either side of the applicator, permit sight of fluid reservoirs 30 (one visible in FIG. 1) within the applicator to monitor progress of refilling operations and facilitate de-bubbling and the like. In use, the surgeon or other user, or operator, will normally draw the applicator across a tissue or other surface to be treated, in the direction of arrow 32, so that vacuum from aspiration tube 12 can prepare the surface for application of fluid from dispensing tube 14, by drawing undesired fluids 34 (or particulate solids) from the tissue surface 11, for example blood, other bodily fluids or excess adhesive. Medical fluid, e.g. a tissue adhesive premixed in the applicator, can be dispensed at a rate controlled by the operator by depressing trigger 22, and applied to tissue surface 11 as drops, droplets or beads or as a linear application 36 or in another pattern, as desired by the user, by suitable manipulation of the applicator. Trigger 22 can be repeatedly depressed to dispense fluid until reservoirs 30 are fully depleted, as indicated by a distinctive audible tone emitted by the device, or indicated visually, by feel, or by other suitable means, the user can remove tip housing 18 and refill the applicator, as described in the parent application.

The embodiment of medical fluid applicator shown in FIGS. 2–5 has a somewhat differently shaped body housing 16 and tip housing 18, but otherwise incorporates the features described in connection with the FIG. 1 embodiment, as indicated by the use of the same reference numerals. Features of the illustrated device that are relevant to the invention as claimed herein, and certain other, but not all features will be here described in detail. Other inventions, subject of one or more patent applications having inventorship common with that of the present application, are embodied in the illustrated embodiment and their embodying structure and operation may or may not be described in detail, herein. Referring to FIGS. 2–5, the applicator shown comprises a valve housing 38 having a suction adapter 39, within suction port 20, which suction adapter 39 is connectable to a suction source (not shown) to apply suction to aspiration tube 12 employing structure in tip housing 18 which is not described here. The suction control valve actuated by button 24 comprises a valve core, a valve shuttle, and other valve elements, as shown in the drawings, or as will otherwise be apparent to those skilled in the art, and which will not be described here in detail, but which enable aspiration tube 12 to be connected with suction adapter 39 and enable dispensing tube 14 to be selectively connected with the mixed output of two medical fluid reservoirs 30 (one of which is shown in FIG. 3) or to the suction source to be cleared of obstructions.

Reservoirs 30, as shown in this embodiment, are cylindrical, tubular containers disposed in parallel, in side-by-side relationship, at the forward end of body housing 16. One reservoir 30 is referenced in FIG. 2. The outer reservoir 30 lies alongside the one shown, behind the plane of the paper. Two fluids contained separately in the reservoirs 30, can be dispensed forwardly via separate fluid pathways through tip housing 18, to a mixing chamber and thence, as a mixture, to dispensing tube 14. Again, this structure is not described in detail here.

Reservoirs 30 can take a variety of forms provided that they can contain the desired fluid, are pressurizable by a suitable actuating mechanism, and are suitably coupled to dispense the contained fluid forwardly. For example, each reservoir 30 may comprise a flexible bulb, or tube, that is directly compressed when engaged by an externally acting member, for example a plunger or lever.

An integrally constructed syringe barrel 40 has a pair of plungers 42 (one shown in FIG. 3) movable in tandem, slidably within reservoirs 30, to pressurize and drive fluid out of reservoirs 30, in response to the user's finger or thumb pressure on trigger 22. Plungers 42 are preferably a close sliding fit in reservoirs 30 to prevent leakage of fluid out of reservoir 30, rearwardly past the plunger 42, for which purpose plungers 42 may bear resilient O-ring seals (not shown), if desired. Such a close fitting plunger naturally offers significant frictional resistance to movement, especially when equipped with seals, and especially if the seals are dry at the beginning of travel. Accordingly, it is desirable for a manually powered, or equivalent, drive mechanism to provide a high mechanical advantage at the beginning of travel, to overcome this resistance.

The plunger drive mechanism shown in the drawings translates the user's effort, as applied to trigger 22, into sliding movement of plungers 42 in reservoirs 30 and comprises, in sequence from trigger 22 to reservoirs 30, an anchor link 44, a trigger link 46, a driving member or pawl 48, a toothed rack 50, and dual plunger 40.

Anchor link 44 is pivotally secured at one end to each side of body housing 16 at pivot points 70 (one shown), and at its other end is coupled by a hinge 52 comprising a pair of pivotal joints (only one is visible in FIG. 3), to one end of trigger link 46. The other end of trigger link 46 is coupled to pawl 48 by a pair of joints 54 (one shown) so that anchor link 44 and trigger link 46 provide a compound lever which translates pivotal drive from trigger 22 into forward lengthwise movement of pawl 48. A tension return spring 55 extends between anchor link 44 and trigger link 46 urging them together and applying a return bias to trigger 22 through engagement of hinge 52 with a platform 60 which extends on the underside of trigger 22.

Pawl 48 has a pawl hook 56 which engages toothed rack 50 and draws it along with pawl 48 in the forward direction of the applicator. Rack 50 has a downward abutment engaging in a pocket in syringe barrel 40 (which structure is to be described) whereby syringe barrel 40 moves forwardly with rack 50, driving plungers 42 along reservoirs 30 to force stored fluid outwardly therefrom for dispensing from dispensing tube 14.

Figure 8:
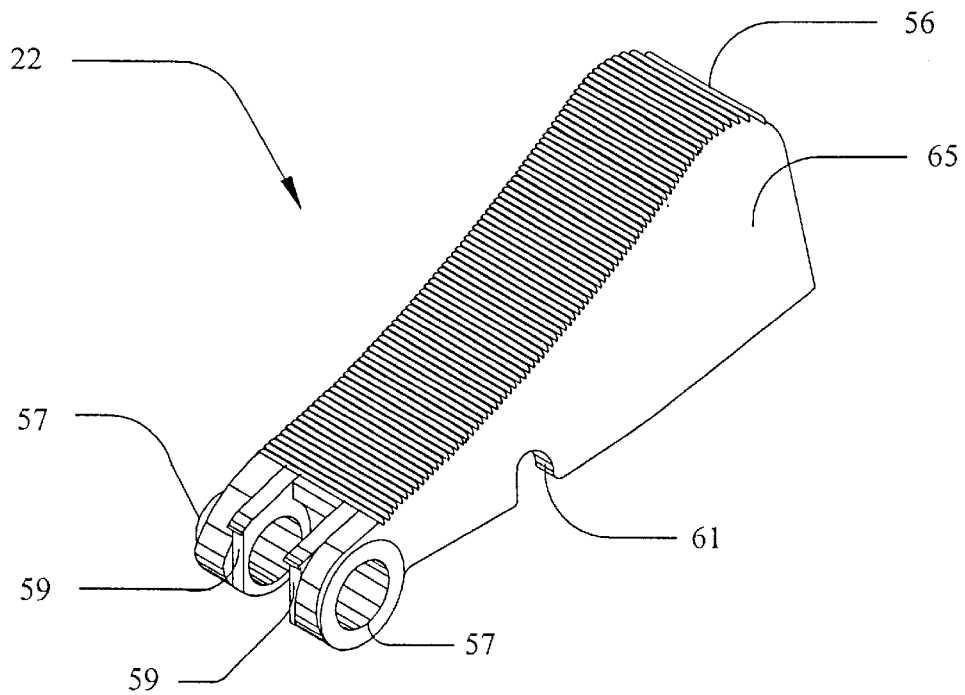
FIG. 8 is a perspective view of the trigger-like actuator button.

Referring additionally to FIG. 8, trigger 22 has a roughly triangular shape, in the plane of FIG. 3, with external ribs 56, or roughening, for grip and feel, and is attached to body housing 16 by a pivot pin 58 at its rearward end where the trigger has bearings 57 to receive pivot pin 58. The forward end of trigger 22 swing about pivot 58 as force is applied to it, and is received downwardly into body housing 16. Platform 60 is located intermediately of the length of trigger 22 and extends in a direction which is forwardly divergent from the general direction of trigger 22's outer surface 65. Rearwardly, platform 60 terminates in a downward abutment 67 (FIG. 3), against which hinge 52 rests in the relaxed (raised) position of trigger 22, in which position, hinge 52 is approximately at the mid-point of the length of trigger 22. Relevant surfaces of platform 60, anchor link 44 and trigger link 46, are suitably smooth, or polished, to reduce friction so that hinge 52 glides across platform 60. Notches 61 (one shown) on either side of trigger 22 constitute travel limiting stops, as will be described. Bearings 57 are formed with adjacent abutments 59 which merge the profile of trigger 22 smoothly with body housing 16 and cover 26, facilitating comfortable operation of the applicator.

Figure 9:
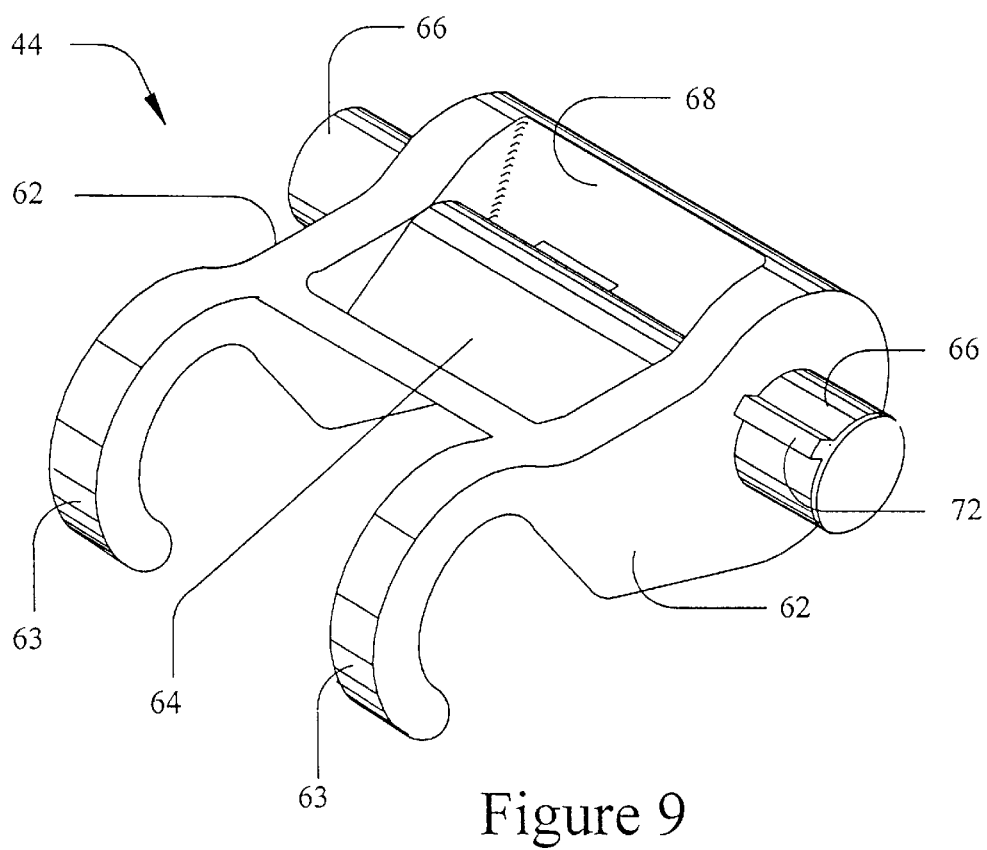
FIG. 9 is a perspective view of an anchor link, being one component of a drive mechanism for the applicator.

Referring to FIG. 9, anchor link 44 comprises a spaced pair of arms 62, each terminating in a rounded hook 63 and which are interconnected by a strengthening web 64. Arms 62 are mounted on a shaft 66 which projects outwardly on either side of hooks 63 and is journalled into either side of body housing 16 at pivot points 70, so that anchor link 44 can pivot, or swing about pivot points 70 (one shown in FIG. 3). Hooks 63 can grasp a rod or the like so that anchor link 44 can be mounted for pivotal movement about both ends of arms 62. A recess 68 accommodates one end of return spring 55 to be secured approximately on the pivot axis defined by pivot points 70. One end of shaft 66 has a key 72 which is a motion stop preventing over-travel and possible binding of the actuator mechanism.

Anchor link 44 is dimensioned for arms 62 to be received within trigger 22, as shown in FIG. 3, and pivot points 70 are disposed in alignment with notches 61 in the sides of trigger 22 whereby notches 61 engage shaft 66 to provide stops, defining the end of trigger 22's downward travel.

Figure 10:
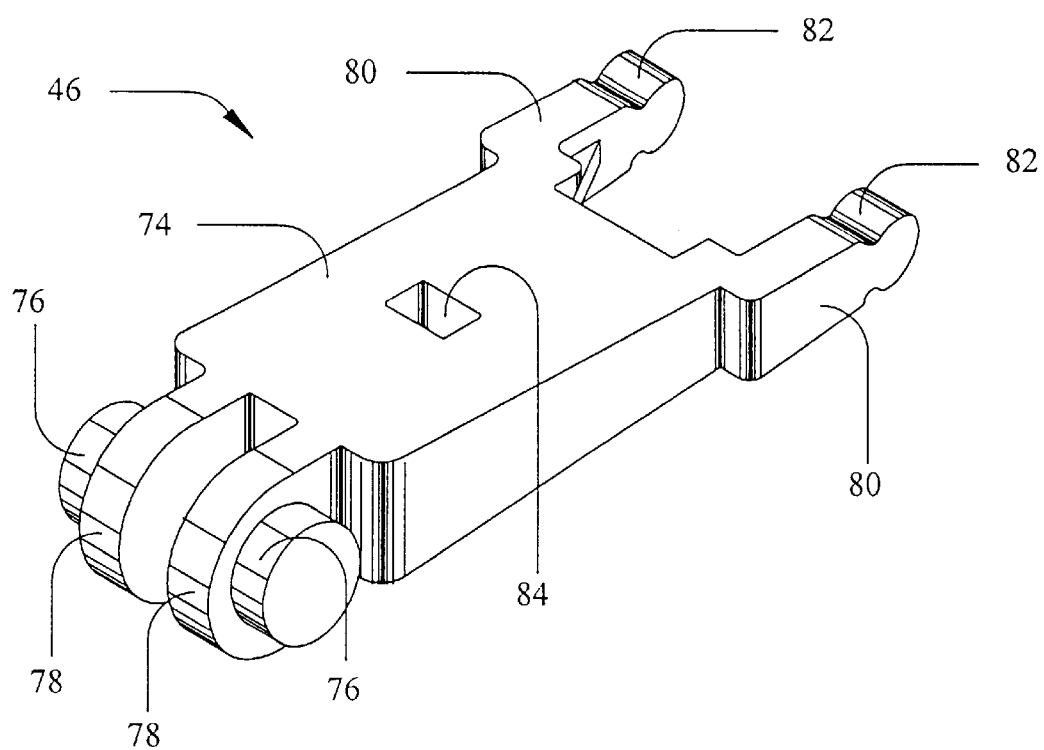
FIG. 10 is a perspective view of a trigger link, being another component of the applicator's drive mechanism.

Referring to FIG. 10, trigger link 46 is also designed to be pivotally mounted at each of its two ends and comprises a central land 74 with a pair of rod-like bosses 76 projecting from flanges 78 at one end and a pair of widely spaced arms 80 at the other end which each terminates in a rounded stub 82. Bosses 76 engage within hooks 63 of anchor link 44 to form two pivoting joints which comprise hinge 52, while stubs 82 engage in mating recesses in pawl 48 (to be described) to form joint 54. A spindle (not shown) within a central opening 84 in land 74 provides a secural point for the other end of return spring 55, which secural point is preferably located approximately at a mid-point between bosses 76 and stubs 82 for optimal leverage.

Anchor link 44 and trigger link 46 are thus, as stated above, coupled together at hinge 52 to form a compound lever secured to the body housing 16 at pivot points 70, which lever unfolds and moves joint 54 with pawl 48 forwardly, as pressure is applied to hinge 52 by depression of trigger 22.

Figure 11:
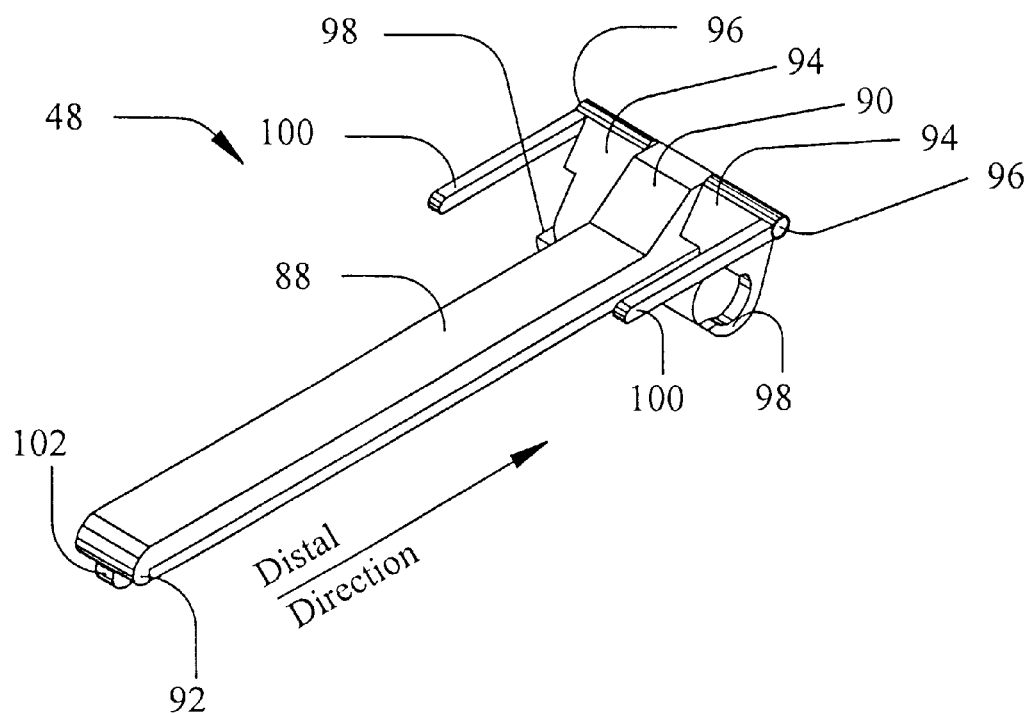
FIG. 11 is a perspective view of a pawl being a further component of the applicator's drive mechanism.
Figure 11A:
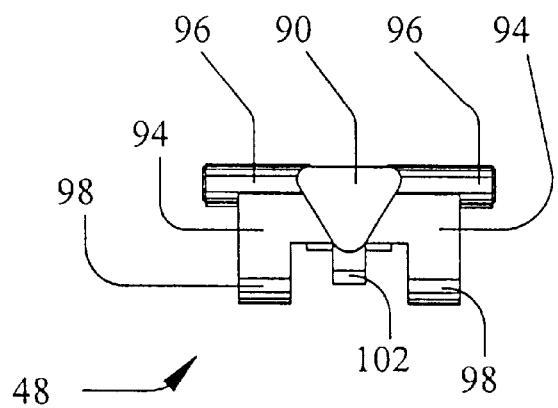
FIG. 11A is an end elevation of the pawl of FIG. 11, looking in the rearward direction.

Referring to FIG. 11, pawl 48 comprises an elongated finger 88 extending from a base 90 in the rearward direction of the applicator and terminating in a rack-engaging pawl hook 92. Either side of base 90 are outriggers 94 each of which has an upper fulcrum pin 96 located above finger 88, and a downwardly depending socket 98 to receive boss 76 of trigger link 46, thereby forming joint 54. Each boss 76 is a snap fit in its respective socket 98, for two-way load transmission.

Figure 13:
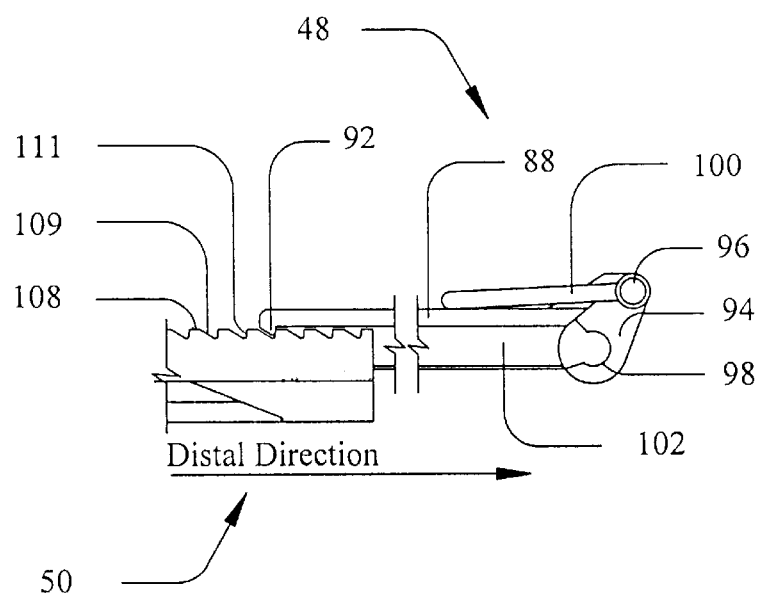
FIG. 13 is a partial side elevational view of the pawl of FIG. 11 engaging with the rack of FIG. 12.

An elongated beam spring 100, which resiliently resists opposed turning forces appled to its ends in a plane passing through the spring, projects rearwardly from each fulcrum pin 96 and is inclined downwardly toward finger 88 (FIG. 13). A guide bar 102 runs beneath finger 88, extending along its length, and is slidingly engageable with a slot in toothed rack 50. Each beam spring 100 is accommodated for sliding movement in a horizontal track 104 located one on each side of body housing 16 (FIG. 3) and acts to rotate pawl finger 88 upwardly at the end of the forward travel of pawl 48, lifting pawl hook 92 and disengaging it from rack 50.

Figure 12:
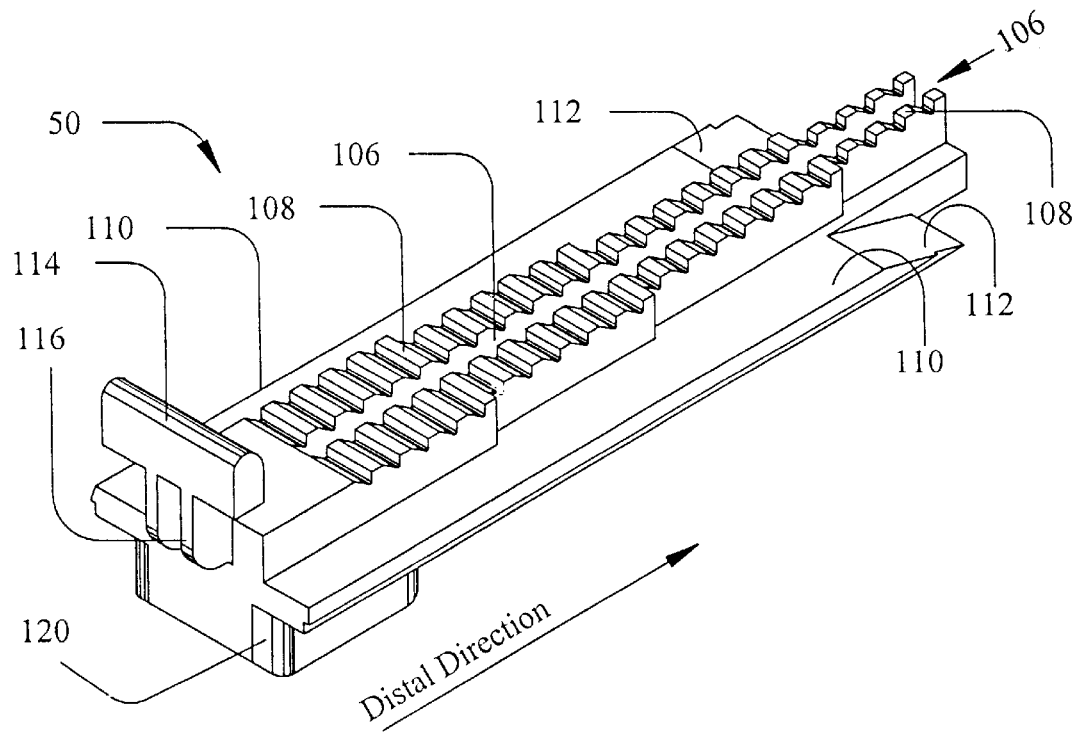
FIG. 12 is a perspective view of a toothed rack being a still further component of the applicator's drive mechanism.

Referring to FIG. 12, rack 50 has a longitudinally extended shape with a central slot 106 to receive guide bar 102, on either side of which central slot 106 are asymmetric patterns of parallel rows of raised teeth 108 extending laterally with respect to the direction of travel of rack 50. As described in more detail, and claimed, in one or more other patent applications with inventorship in common with the present application, patterns of teeth 108 interact with patterns of fixed strikers (not shown) to generate a sequence of audible indicator tones, as rack 50 moves forwardly, which tone sequence audibly indicates the extent of depeletion of reservoirs 30 to the user (and others nearby). To either side and below the patterns of teeth 108, are side pieces 110 which support rack 50 for sliding movement in body housing 16 in grooves or recesses (not shown). Side pieces 110 terminate forwardly in cam surfaces 112 which engage sockets 98 of pawl 48 at the end of the travel of rack 50 and lift pawl hook 92 out of engagement with teeth 108. Being thus disengaged by pawl 48, rack 50 has freedom of movement in body housing 16, after opening hinged cover 26, permitting its removal from body housing 16, to disassemble the applicator or, more importantly, permitting manual withdrawal of rack 50, by sliding it rearwardly in the housing grooves, to refill the reservoirs 30 with fluid, using a mating filling device, for example as described in the parent and other related applications.

FIG. 13 shows, in profile, one possible shape of pawl hook 92 on pawl 48, namely triangular,, and a corresponding engaging profile of teeth 108 of rack 50, each of which has a sloping forward face 109 and a perpendicular rearward face 111. Forward movement of pawl 48 or rearward movement of rack 50 maintains engagement of pawl hook 92 with rack teeth 108, transmitting any motion from one drive member to the other while opposite relative motion provokes disengagement.

At its rearward end, rack 50 carries an upstanding, indicator bar 114, optionally marked with an indicator line 115, which indicator bar 114 is supported on a buttress 116 to extend transversely of the rack 50. The structures of indicator bar 114 and support buttress 116 are relatively sturdy to provide a grip for manual removal of toothed rack 50 from body housing 16. Depending downwardly from the rearward end of rack 50 is a block-shaped key 120 which is received in a pocket 122 in dual syringe 40 (FIG. 15) and couples syringe barrel 40 to rack 50 for two-way movement therewith, longitudinally of body housing 16. Such coupling enables refilling of reservoirs 30 by rearward withdrawal of rack 50 from a forwardly advanced position, by gripping indicator bar 114, to draw new aliquots of fluid into reservoirs 30, for example, as described in parent application Ser. No. 08/838,078.

Figure 14:
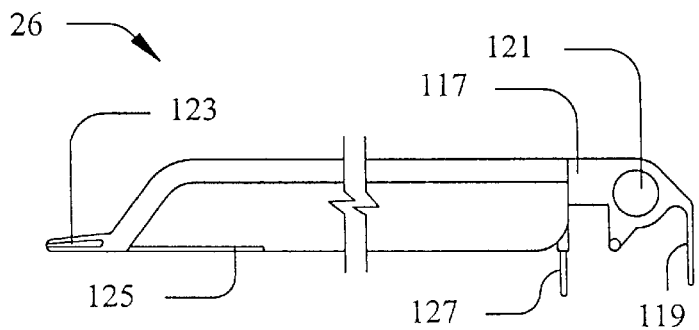
FIG. 14 is a side elevational view of a hinged access cover being a component for the applicator shown in FIGS. 2–5.
Figure 14A:
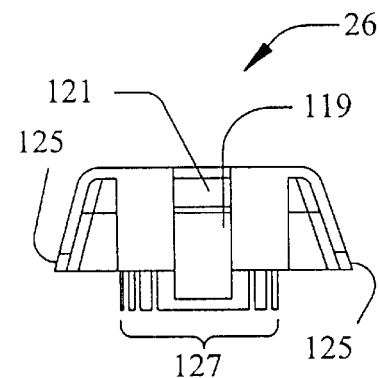
FIG. 14A is an end elevational view of the cover shown in FIG. 14, viewed from a forward end of the applicator, being the righthand end as viewed in FIG. 14.

Referring to FIGS. 14–14A, and FIGS. 2–3, cover 26 extends generally longitudinally over a rearward portion of the applicator, just rearwardly of reservoirs 30 and overlying most of the extent of toothed rack 50 when in its most rearward position (with reservoirs 30 filled). Cover 26 has a forward extension 117 which carries hinge structure 121, mountable on pivot pin 58 to provide cover 26 with a hinge connection to body housing 16 and which extension terminates in a centrally disposed downward tab 119 (FIG. 14A).

A rearward, horizontally extending tab 123, and side lips 125, adjacent tab 123, provide convenient lifting means for opening cover 26, which, if desired, can be a snap fit with body housing 16 (employing structure not shown).

Depending from the forward end of cover 26 is an array of strikers or tone emitter 127 which engage teeth 108 as rack 50 is advanced forwardly, emitting various tones, as described in one or more copending applications with common inventorship. Referring additionally to FIG. 13, tone emitter 127 is structured and configured to be sufficiently deformable to ride up sloping forward face 109 of each rack tooth 108, yet sufficiently rigid to act as a locking pawl, locking against rearward face 111 of each rack tooth 108 and preventing rearward movement of rack 50, assisting in the prevention of flowback or drawback.

Figure 14B:
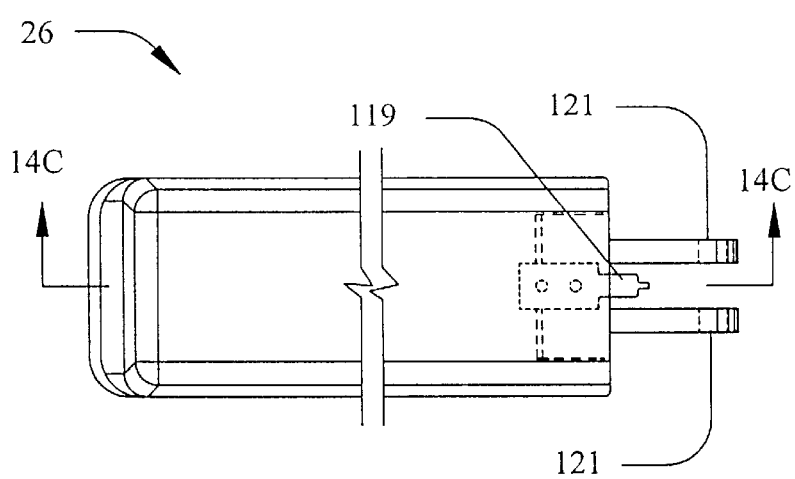
FIG. 14B is a plan view of an alternative hinged access cover.

Tab 119 is preferably resilient and configured to be engaged by finger 88 of pawl 48 to urge pawl hook 92 downwardly to interdigitate with rack teeth 108, for which purpose, the rearward, upper surface, referenced 93 in FIG. 13, of pawl finger 88 is curved or chamfered to promote resilient deformation of tab 119 as it is engaged by pawl finger 88. The limit of pawl 48's rearward travel is such that it does not foul tone emitter 127. In the alternative construction of cover 26 depicted in FIGS. 14B–14D, wherein parts with similar functionality bear similar reference numerals although they may have a different configuration from their configurations in the embodiment shown in FIGS. 2–3 and 14–14A, downward tab 119 and tone emitter 127 are embodied in a one-piece resilient clip 131 which is press fitted to projections 131 at the forward end of a plastic cover body 133 which are engaged by apertures 136. This construction provides additional design options enabling greater resilience and durability to be built into tab 119 and tone emitter 127 by forming clip 131 of a different material from cover body 133, for example spring steel or the like. As shown, tab 119 is curved backwardly, the better to engage pawl finger 88 and urge it downwardly to interdigitate pawl hook 92 with rack teeth 108. tone emitter 127 as shown in FIG. 14D is configured as a single rectangular sounding board, or resonance plate, extending approximately across the width of rack 50, and having sufficient rigidity to generate audible sonic vibrations when struck by one or more rack teeth 108.

Figure 14D:
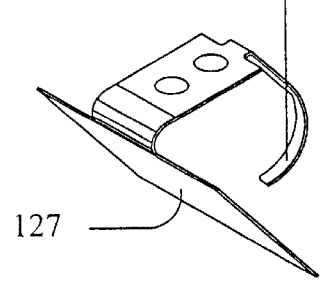
FIG. 14D is a perspective view of a spring clip component of the cover shown in FIGS. 14B and 14C.
Figure 14C:
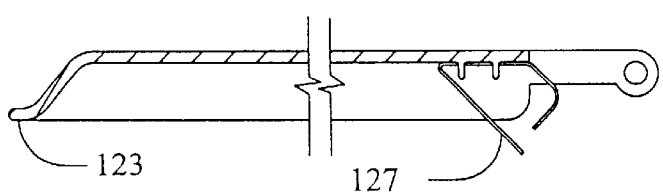
FIG. 14C is a section on the line 14C—14C of FIG. 14B.

The volume and other acoustic characteristics of the generated sound can be varied by suitable variations in the shape, area, thickness, and other characteristics of tone emitter 127, which can also be digitated, as shown in FIG. 14A, in the integral clip construction of FIG. 14D, if desired. As shown, tone emitter 127, can with this clip design, be angled sharply forwardly to lock positively against rack teeth 108, preventing rearward movement of rack 50 until cover 26 is opened.

Figure 2:
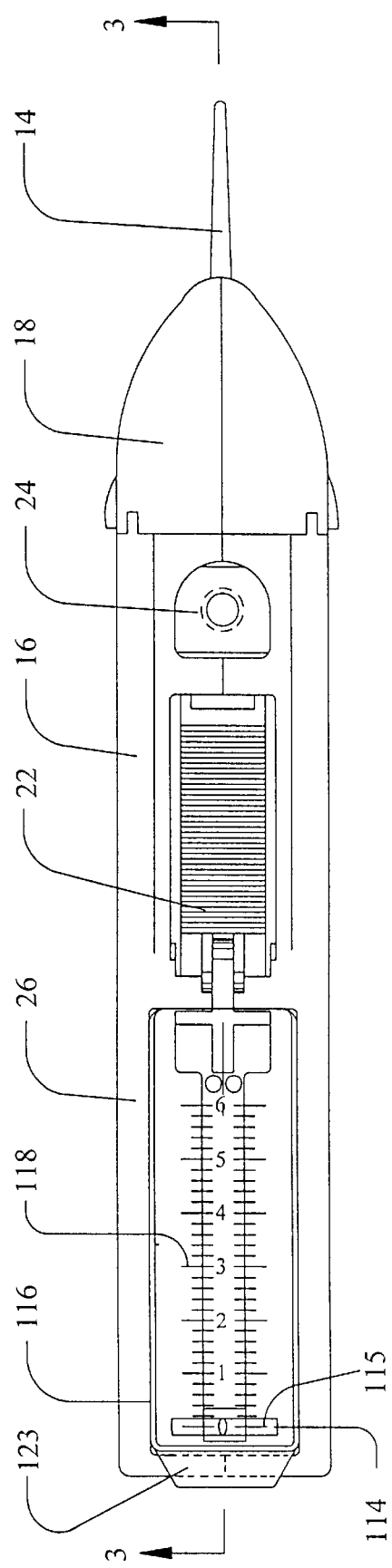
FIG. 2 is a plan view of another embodiment of medical fluid applicator which has close external similarity to the embodiment of FIG. 1.
Figure 3:
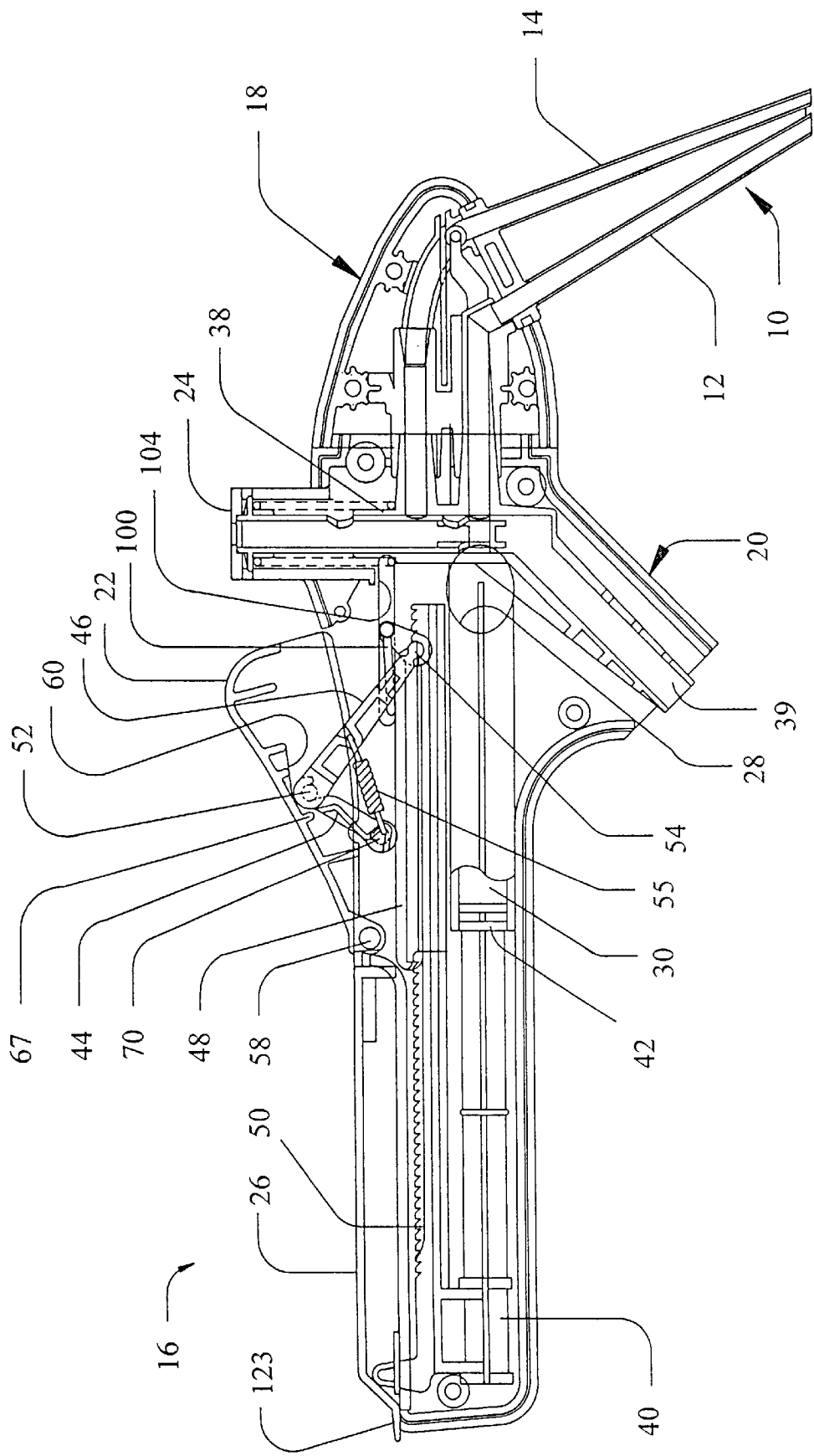
FIG. 3 is a sectional view on the line 3—3 of the applicator shown in FIG. 2.
Figure 5:
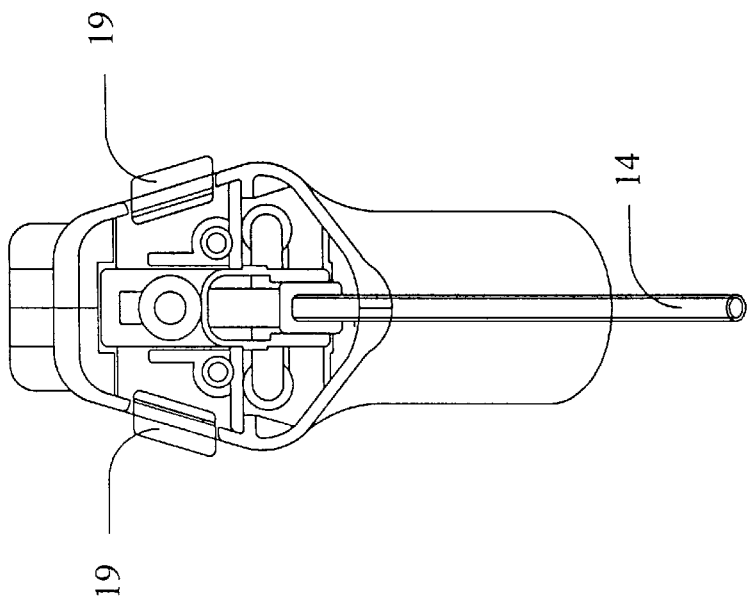
FIG. 5 is a righthand, or front, end elevational view of the applicator shown in FIGS. 2 and 3.
Figure 4:
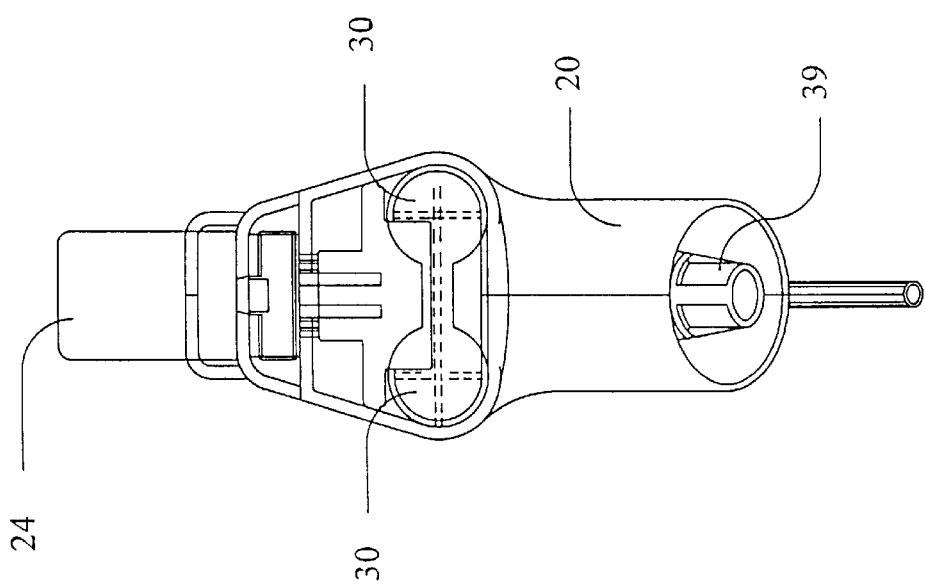
FIG. 4 is a lefthand, or rear, end elevational view of the applicator shown in FIGS. 2 and 3.

Hinged cover 26 is translucent or transparent and preferably carries a scale 118 against which travel of indicator bar 114 may be viewed and gauged (FIG. 2). Since plungers 42 are linearly coupled to rack 50, as will be described, travel of indicator bar 114 viewed against scale 116 is indicative of travel of plungers 42 in reservoirs 30 and thence of the quantities of fluids dispensed from reservoirs 30. Opening cover 26 swings tone emitter 127 out of engagement with rack 50 and tab 119 out of engagement with finger 88 of pawl 48.

Figure 15:
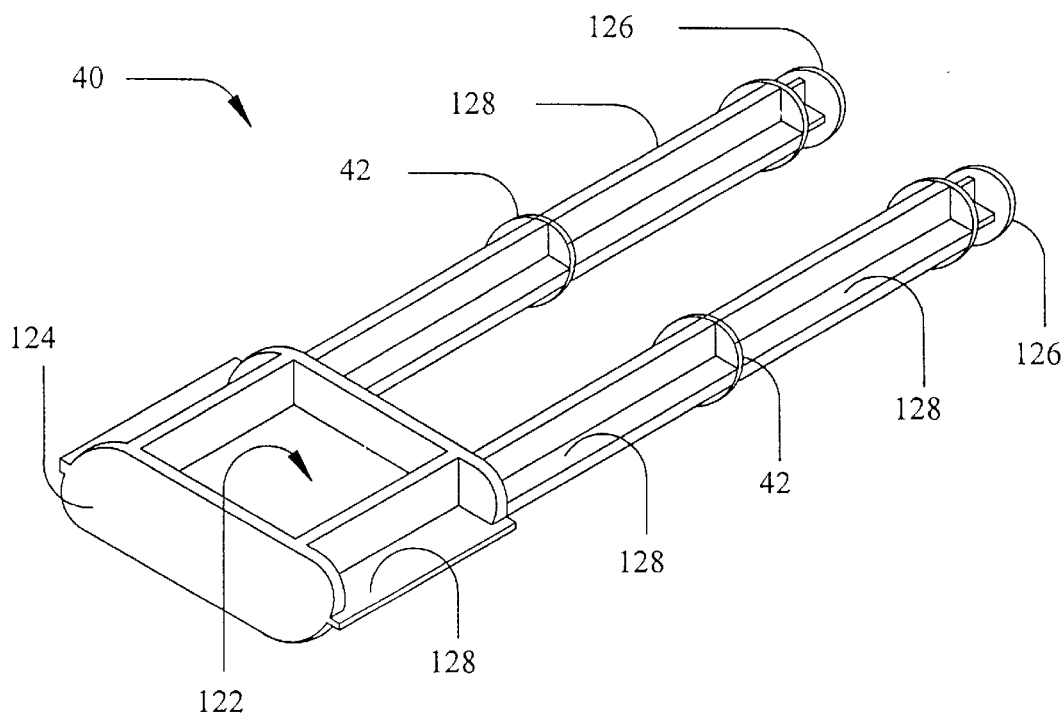
FIG. 15 is a perspective view of a dual syringe being a still further component of the applicator's drive mechanism.

Referring to FIG. 15, pocket 122 in dual syringe 40 is formed in a base 124 from which plungers 42 extend forwardly to have fluid engaging forward ends 126 in reservoirs 30, which ends 126 may bear peripheral seals, or O-rings, although such seals are not shown. Plungers 42 are molded with strengthening splines 128.

Figure 16:
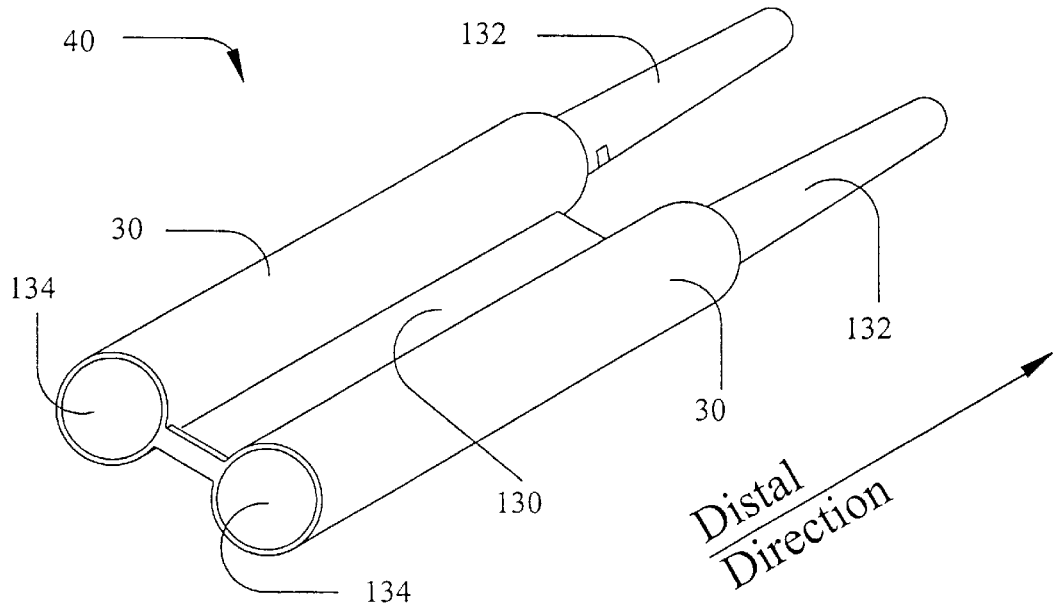
FIG. 16 is a perspective view of a syringe barrel comprising two fluid reservoirs, being a still further component of the inventive applicator.

Referring to FIG. 16, syringe barrel 40 is formed in one piece with a web 130 joining the two reservoirs 30 which are here shown as being cylindrical, a preferred configuration, and a circular section which is optional but convenient. Reservoirs 30 terminate in nozzles 132 at their forward ends through which suitable fluids may be discharged in use or received during refilling. The rearward ends of reservoirs 30 have open ports 134 to receive plungers 42 for longitudinal travel in the reservoir. Preferably, plungers 42 directly contact fluid in reservoirs 30 so that no additional barrier or transverse divider prevents fluid being drawn into one or both reservoirs 30 by rearward retraction of plungers 42 during refilling. However, in alternative constructions, for example, constructions employing disposable fluid cartridges, the cartridge will have a rearward end wall separating plunger 42 from the cartridge's fluid contents, so that refilling by plunger withdrawal may not be appropriate.

A wide range of fluids can be accommodated in reservoirs 30 for dispensing and applying with the novel applicator described herein, and of particular interest are those having medical or biological uses, for example, tissue adhesives used for wound or spatial closure or for prosthetic attachment or to provide substrates for delivery of biologically or medically active materials e.g. microencapsulated locally acting drugs, nutrients or other actives. The applicator is particularly well suited to dispensing a two component interactive fluid system such as a two-component adhesive system, especially where the unmixed components have relatively low viscosity, as compared, for example with a two-component epoxy resin and hardener system. Examples of such lower viscosity fluid systems include two-component tissue adhesive systems, especially fibrin adhesive systems such as described in parent application Ser. No. 08/838,078 which comprise a fibrin component and a thrombin component, and synthetic equivalents thereof, as known to those skilled in the art.

Also, if desired, the applicator may be used to deliver single or multi-component systems for other purposes, e.g. to prevent tissue adhesion, for example in abdominal surgery, anastomosis or other surgery.

Most components of the novel applicator can be rendered as plastics moldings from resin or polymer materials, the choice of suitable ones of which will be apparent to those skilled in the art, as will alternative materials such as metal alloys, sinters or the like. Some examples of suitable polymer materials are: for the toothed rack 50, the pawl 48, the trigger link 46, the anchor link 44, the syringe barrel 40, a polyetherimide, such, for example, as General Electric Company's ULTEM (trademark) 1000 resin; for the trigger 22, the cover 26, the valve button 24, the body housing 16, the tip housing 18, and ABS (acrylonitrile-butadiene-styrene) resin, such, for example, as Bayer AG's LUSTRAN 648 (trademark) resin; and for aspiration tube 12, dispensing tube 14 and syringe barrel 40 a polypropylene, such for example as Montel's PRO-FAX SR-857M (trademark).

While dimensions are not critical, and embodiments not suitable for holding in one or both hands, are contemplated, one embodiment that is particularly well suited for use by a surgeon, which is comfortable, lightweight and precisely manipulable, has a body length of the body housing 16 (without tip housing 18) of about 6 inches (about 15 cm) and a length of reservoirs 30 of about 2¼ inches (about 5.5 cm) with a corresponding extent of the toothed area of rack 50 sufficient to accommodate a travel of about 2¼ (about 5.5 cm). With circular cylindrical reservoirs 30 of approximately ⅜ inch (0.9 cm) diameter the reservoir capacity is about 3 cc, each, total 6 cc with two reservoirs 30. Such dimensions as these provide an applicator which is comfortable and ergonomic for most surgeons to use with precision. Preferred constructions may vary these dimensions by up to about 10, or preferably 20 percent. Less demanding applications may vary the given or corresponding dimensions by up to about 50 percent while still providing an applicator that can be supported and properly manipulated in one hand.

The operation of the drive mechanism is as follows. In the rest (raised) position of trigger 22, the influence of return spring 55 acting on trigger link 46 causes beam spring 100 to lie flush in track 104 so that hook 92 of pawl 48 is raised clear of toothed rack 50.

Trigger 22 can be repeatedly depressed, until rack 50 is fully advanced forwardly and reservoirs 30 are fully depleted. Trigger 22 is returned to its raised, rest position by return spring 55 when released, and its travel may be described as having a downward stroke and a return stroke, the downward stroke being further described as having a commencement phase and a completion phase. When trigger 22 is initially depressed, in the commencement phase of the downward stroke, by a user, or possibly, by mechanical or electrical actuation, force applied along trigger link 46 to joint 54 pivots the joint about fulcrum pins 96, opening up the angle between beam spring 100 and socket 98, while working against the resilient action of beam spring 100. Initially, hook 90 moves downwardly to engage toothed rack 50, and beam spring 100 lies flush in track 104.

Further movement of trigger 22, in the completion phase of the downward stroke advances pawl 48 forwardly, drawing rack 50 along with it, as pawl hook 92 engages with rack teeth 108 and sounding tone emitter 127 as it rides over rack teeth 108. Rack 50 is interengaged with dual syringe 40 by key 120 locking in pocket 122, so that dual syringe 40 is also advanced forwardly, driving plungers 42 forwardly in reservoirs 30 to dispel fluid therefrom. The completion phase of the stroke terminates either when the force exerted by the user on trigger 22 is inadequate to advance plungers 42, or notches 61 in the sides of trigger 61 engage shaft 66 stopping the trigger's travel. While the user maintains pressure on trigger 22, flowback is prevented by interengagement of dual syringe 40 with rack 50 and of rack teeth 108 with hook 92.

When the trigger is released, beam springs 100 promptly act to rotate pawl 48 and raise pawl hook 92, disengaging it from rack 50 while return spring 55 pulls trigger link 46 toward anchor link 44, raising trigger 22 and carrying pawl 48 rearwardly, in preparation for a repeat stroke, with pawl hook 92 travelling silently, clear above teeth 108 to its rearmost position under cover tab 119 where it is biased downwardly to be fully engaged with rack teeth 108. Meanwhile, as previously stated, tone emitter 127 holds rack 50 against rearward motion. Accordingly, cover 26 may be opened, pivoting tone emitter 127 out of engagement with rack 50 and freeing pawl finger 88 from engagement with tab 119, tip housing 18 can be removed and reservoirs 30 may be refilled from a suitable mating fluid supply system (such for example as described in parent application Ser. No. 08/838,078) by withdrawing indicator bar 114, by hand, in the rearward direction.

Figure 6:
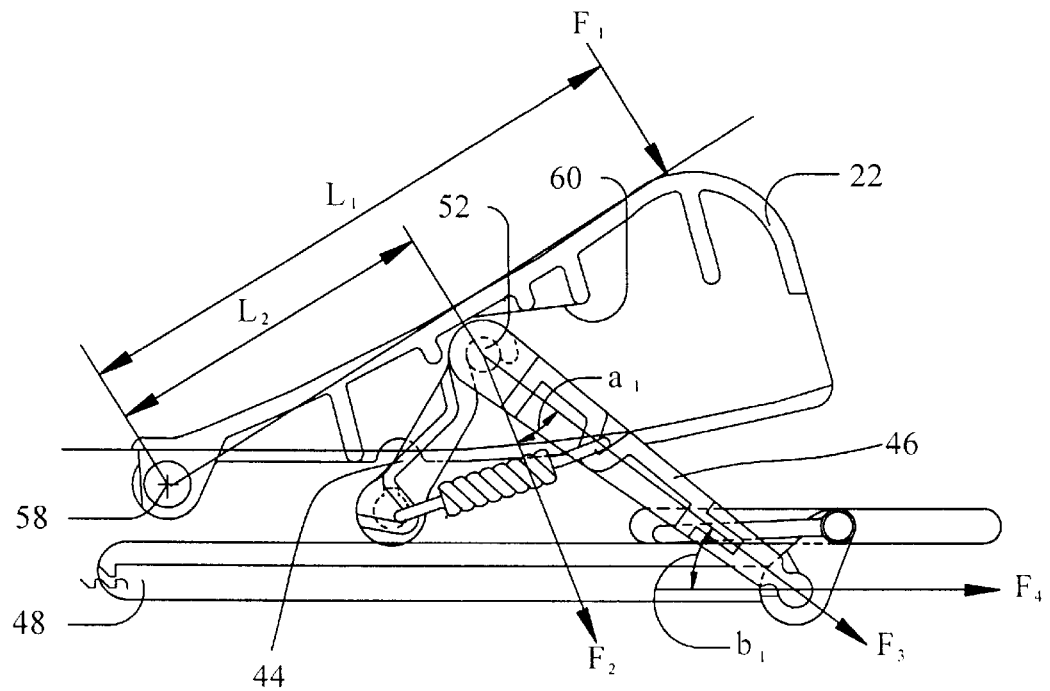
FIG. 6 is an enlarged view of a portion of FIG. 3, showing a trigger-like actuator button in a rest position.
Figure 7:
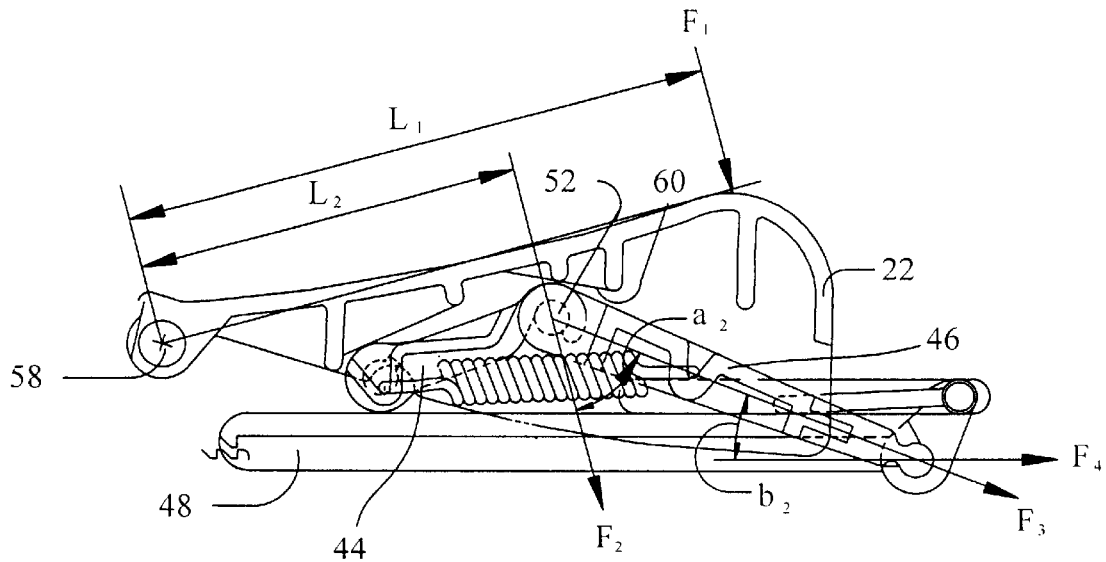
FIG. 7 is a view similar to FIG. 6 showing the trigger-like actuator button fully depressed.

Referring to FIGS. 6 and 7, some of the forces that come into play when a user depresses trigger 22 are shown symbolically for illustration purposes and to model the operation of this one embodiment of the inventive applicator drive mechanism. Other vector analyses and descriptions can be made, as will be apparent to those skilled in the art, and the invention is not dependent upon the accuracy, in practice, of the conclusions reached, bearing in mind, in particular, the several assumptions and approximations that are necessarily made. The following description is included to assist in understanding the invention and in applying the teachings herein to the practice of the invention.

The manual (or other) force which a user applies to the trigger is assumed to be suitably represented as a force $F_1$ at a distance $L_1$ from trigger pivot pin 58, which will generate a moment $F_1 \cdot L_1$ about pivot pin 58. Ignoring frictional and other losses, platform 60 engaging hinge 52 translates the received impulse into a force $F_2$ in a direction perpendicularly about pivot pin 58 at a distance $L_2$ from pivot pin 58, which distance is determined by the location of platform 60, such that the moments are equal, i.e. so that $$F_1 \cdot L_1 = F_2 \cdot L_2$$

and $$F_2 = F_1(L_1/L_2)$$

There is accordingly a mechanical advantage whereby force $F_2$ is amplified by the ratio of the length $L_1$ to length $L_2$. Thus, a designer, or engineer, can increase his advantage by increasing length $L_1$ of trigger 22, or by decreasing the distance $L_2$ of platform 60 from pivot 58, which decrease will, however, decrease the distance traveled by pawl 48 on each stroke of trigger 22.

Force $F_3$ transmitted along trigger link 46, from the point of contact of platform 60 with pivot 52 to joint 54, will be $F_2 \cos \alpha$ where $\alpha$ is the angle between the directions of forces $F_2$ and $F_3$. (The cosine value of course diminishes with increasing angle, though not proportionately.) Force $F_4$ exerted on pawl 48, in its direction of travel, will be $F_3 \cos \beta$ where $\beta$ is the acute angle between the directions of forces $F_3$ and $F_4$. Substituting for $F_2$ and $F_3$, it follows that $$F_4 = F_1(L_1/L_2) \cos \alpha \cos \beta.$$

As stated above, this conclusion necessarily makes approximation s and assumptions.

The performance characteristics of the drive mechanism are greatly dependent upon the location and nature of the connection between trigger link 46 and trigger 22. In mechanisms such as those described in parent application Ser. No. 08/838,078 a trigger link (lever arm 110 therein) is pivotally attached to trigger 22 (105) at a point relatively distant from pivot 58, providing a modest mechanical advantage which, depending upon the particular geometry employed, tends to increase as trigger 22 is depressed, because the product of cos α and cos β increases. Thus angle β decreases more quickly than can be compensated for by increases in angle β and the corresponding diminishment of its cosine.

It would be desirable to provide a greater mechanical strength in the commencement phase of the stroke to more readily overcome initial frictional losses, or sticking, and inertia, and provide smoother performance and feel. The mechanical advantage can be increased by relocating the point of attachment of trigger link 46 to trigger 22 to be closer to pivot pin 58. A difficulty with this solution is that the possible degree of travel of joint 54, and thence pawl 48, is significantly reduced. Another difficultly is that angles α and β have unfavorable values where further travel of trigger 22 results in an increase in the product of their cosines, increasing the mechanical advantage. Such an increase in mechanical advantage adversely affects the controllability of the applicator and may cause fluid to spurt out unintentionally.

The invention solves these problems by decoupling trigger link 46 from trigger 22, securing it to pivoted anchor link 44, and allowing hinge 52 to float or glide on platform 60 in a direction away from the pivot axis through pivot pin 58. The commencement phase of a trigger actuation stroke provides an excellent mechanical advantage as hinge 52, at the rearward end of platform 60 is engaged by both platform 60 and abutment 67, applying a driving force along trigger link 46. At this point, FIG. 6, $L_2$ is relatively small, perhaps one half of $L_1$, angle $\alpha_1$ is small and angle $\beta_1$ has an intermediate value. As the downward trigger stroke continues with its completion phase, hinge 52 moves forwardly along platform 60 increasing length $L_2$ and increasing angle $\alpha_2$ which effects together reduce the mechanical advantage and, with suitable choices for the length and positioning of anchor lever 44, can be sufficient to overcome the effect of the concomitant increase in angle β. The characteristics of tension spring 55 are selected to provide a suitable resistance and to ensure that it provides a satisfactory recovery means, returning the trigger actuation mechanism to its rest position.

The result is a diminishing mechanical advantage, a good feel to the trigger action and an applicator which can be accurately controlled and used to dispense and apply small quantities of fluid precisely to desired locations. Such mechanism is of particular value for a tissue adhesive applicator for surgical and microsurgical uses.

These beneficial results are at least partly attributable to the use of a sliding pivot, 54, which has come limited freedom of translational movement relative to trigger 22 as opposed to simply being pivotally attached to trigger 22. This freedom of movement is provided by the cooperative action of anchor link 44 and platform 60. As illustrated, in exemplary fashion, anchor link 44 can be approximately half the length of trigger link 46 and its pivot point 70 of attachment to body housing 16 can be vertically between pivot in 58 and joint 54, and displaced a small distance rearwardly from abutment 67 so that anchor link 44 is canted forwardly in the rest position.

Other constructions which provide some or all of the benefits of the invention will be apparent to those skilled in the art in the light of the teachings herein. For example, trigger 22 could be button-like with a linear reciprocal travel into body housing 16 while having cam surfaces to provide desired lateral travel of hinge 52. Other means can be provided to guide the upper rearward end of trigger link 46. Thus, it could bear one or more projections running in suitably shaped grooves or tracks in trigger 22. Pawl 48 could be replaced by a friction roller engaging an extension of rack 48, though adjustments to the geometry or means to accommodate the extension would be desirable. Similarly, pawl 48 might engage rack 50 frictionally.

INDUSTRIAL APPLICABILITY

The present invention is particularly suitable for application in the surgical devices and medical or veterinary treatment industries, but has wide application in many industries where controlled application of small quantities of one or more fluids is desirable.

While some illustrative embodiments of the invention have been described above, it is, of course, understood that various modifications and equivalents of the described embodiments will be apparent to those of ordinary skill in the art. Some equivalents will be readily recognized by those of ordinary skill while others may require no more than routine experimentation. Such modifications and equivalents are within the spirit and scope of the invention, which is limited and defined only by the appended claims.

We claim:

1. A manually actuated fluid applicator having:
   a) a fluid container to contain fluid;
   b) a movable actuator having an actuator stroke and being repeatedly operable by a manually applied force on the movable actuator to dispense fluid from the applicator by displacement of fluid from the fluid container, the actuator stroke having a commencement phase and a completion phase; and
   c) a drive mechanism to translate the manually applied force on the movable actuator to a fluid displacing force exerted on fluid in the fluid container;

wherein the mechanical advantage of the drive mechanism with regard to the ratio of the fluid-displacing force to the manually applied force is proportionately larger in the commencement phase and smaller throughout the completion phase.

2. An applicator according to claim 1 wherein the mechanical relationships in the commencement and the completion phases respectively are such as to overcome initial frictional and inertial resistance and provide a smooth feel of the actuator throughout the stroke.

3. An applicator according to claim 1 wherein the actuator comprises a manually engageable and depressible actuator member, a driving member and a pivoted link having one end pivoted to the driving member and having another end, the applicator further comprising a driving connection between the depressible actuator member and the other end of the pivoted link the driving connection providing freedom of movement of the other end of the pivoted link with respect to the depressible actuator member in a direction to reduce the proportion of drive force transmitted as the stroke advances.

4. An applicator according to claim 3 wherein the depressible actuator member comprises a trigger pivotal about a pivot axis and the driving connection comprises a driving surface on the trigger slidingly engageable with the other end of the pivoted link, the driving surface being disposed to urge the other end of the pivoted link to move away from the pivot axis as the trigger is moved pivotally.

5. An applicator according to claim 4 wherein the drive mechanism comprises an anchor link having one end pivotally anchored and another end coupled to the other end of the pivoted link to provide a hinge, said hinge being slidingly engageable with the driving surface on the trigger.

6. An applicator according to claim 1 wherein the applicator is a plural fluid applicator having a plurality of fluid containers respectively for a plurality of fluids and wherein the drive mechanism acts on fluids in the fluid containers in harness to exert a fluid displacing force on each fluid simultaneously.

7. An applicator according to claim 6 wherein each said fluid container is a cylindrical reservoir, the drive mechanism comprises a plurality of plungers slidable one in each said reservoir, with a linear motion, to exert said fluid displacing forces on fluid in the fluid container, a longitudinally extended toothed rack movable in tandem with the plungers and a driving member having a hook engageable with the toothed rack and driven cyclically by said movable actuator in a direction linearly along the toothed rack to advance the rack incrementally with each advance stroke of the movable actuator and to disengage and withdraw the driving member in the opposite direction along the toothed rack on a retraction stroke of the movable actuator, whereby successive strokes of the movable actuator progressively advance the toothed rack.

8. An applicator according to claim 7 wherein the driving member comprises an elongated pawl pivotally movable transversely of the rack to engage with and disengage from the rack.

9. An applicator according to claim 1 wherein the movable actuator comprises a pivoted trigger and the drive mechanism comprises a trigger link, an anchor link and a driving member movable in the direction of displacement of fluid from the fluid container, wherein the trigger link has one and another end, the one end being in sliding engagement with the pivoted trigger and the other end being pivotally attached to the anchor link and wherein the anchor link is pivotally secured to the applicator.

10. An applicator according to claim 1 wherein the drive mechanism operates without lost motion between the manual actuator and the fluid displacing force exerted on the fluid in the fluid container.

11. An applicator according to claim 10 wherein the drive mechanism comprises a dispelling member to dispel fluid from the fluid container and the drive mechanism maintains constant engagement from the manual actuator to the dispelling member.

12. An applicator according to claim 10 wherein the drive mechanism comprises a dispelling member to dispel fluid from the fluid container and the drive mechanism maintains provides a two-way connection between the manual actuator and the dispelling member whereby fluid can be dispelled from or drawn into the fluid container.

13. A manually actuated plural fluid applicator having:
a) a plurality of fluid containers respectively to contain a plurality of fluids one to each container;
b) a movable actuator having an actuator stroke and being repeatedly operable by a manually applied force on the movable actuator to dispense fluid from the applicator by displacement of fluid from the fluid container, the actuator stroke having a commencement phase and a completion phase; and
c) a drive mechanism to translate the manually applied force on the movable actuator to act on fluids in the fluid containers in harness to exert a fluid displacing force on each fluid simultaneously;

wherein the mechanical advantage of the drive mechanism with regard to the ratio of the fluid-displacing force to the manually applied force is proportionately larger in the commencement phase and smaller throughout the completion phase, the mechanical relationships in the commencement and the completion phases respectively being such as to overcome initial frictional and inertial resistance and provide a smooth feel of the actuator throughout the stroke;

wherein the actuator comprises a manually engageable and depressible actuator member, a driving member and a pivoted link having one end pivoted to the driving member and having another end, the applicator further comprising a driving connection between the depressible actuator member and the other end of the pivoted link the driving connection providing freedom of movement of the other end of the pivoted link in a direction to reduce the proportion of drive force transmitted as the stroke advances;

wherein the depressible actuator member comprises a trigger pivotal about a pivot axis and the driving connection comprises a driving surface on the trigger slidingly engageable with the other end of the pivoted link, the driving surface being disposed to urge the other end of the pivoted link to move away from the pivot axis as the trigger is moved pivotally;

wherein the drive mechanism comprises an anchor link having one end pivotally anchored and another end coupled to the other end of the pivoted link to provide a hinge, said hinge being slidingly engageable with the driving surface on the trigger; and wherein each said fluid container is a cylindrical reservoir, the drive mechanism comprises a plurality of plungers slidable one in each said reservoir, with a linear motion, to exert said fluid displacing forces on fluid in the fluid container, a longitudinally extended toothed rack movable in tandem with the plungers and a driving member engageable with the toothed rack and driven reciprocally by said movable actuator in a direction linearly along the toothed rack to advance the rack incrementally with each stroke of the movable actuator.

14. A manually actuated fluid applicator having:
a) a fluid container to contain fluid;
b) a movable actuator repeatedly operable by a manually applied force to dispense fluid from the applicator by displacement of fluid from the fluid container, the actuator stroke having a commencement phase and a completion phase; and
c) a drive mechanism to translate the manually applied force on the movable actuator to a fluid displacing force exerted on fluid in the fluid container;

wherein the actuator comprises a manually engageable and depressible actuator member, a driving member and a pivoted link having one end pivoted to the driving member and having another end, the applicator further comprising a driving connection between the depressible actuator member and the other end of the pivoted link the driving connection providing freedom of movement of the other end of the pivoted link in a direction to reduce the proportion of drive force transmitted as the stroke advances.

15. An applicator according to claim 14 for depositing fluid adhesive on a work surface wherein the driving connection comprises a driving surface on the actuator member slidingly engageable with the pivoted link.

16. An applicator according to claim 15 wherein the drive mechanism provides constant engagement between the manual actuator and the fluids without lost motion.

17. A manually actuated plural fluid applicator having:
a) a plurality of fluid containers respectively to contain a plurality of fluids one to each container;
b) a movable actuator repeatedly operable, with an actuator stroke effected by a manually applied force on the movable actuator, to disperse fluid from the applicator by displacement of fluid from the fluid container, the actuator stroke having a commencement phase and a completion phase; and
c) a drive mechanism to translate the manually applied force on the movable actuator to act on fluids in the fluid containers in harness to exert a fluid displacing force on each fluid simultaneously;

wherein each said fluid container is a cylindrical reservoir, the drive mechanism comprises a plurality of plungers slidable one in each said reservoir, with a linear motion, to exert said fluid displacing forces on fluid in the fluid container, a longitudinally extended toothed rack movable in tandem with the plungers and a driving member having a hook engageable with the toothed rack and driven cyclically by said movable actuator in a direction linearly along the toothed rack to advance the rack incrementally with each advance stroke of the movable actuator and to disengage and withdraw the driving member in the opposite direction along the toothed rack on a retraction stroke of the movable actuator, whereby successive strokes of the movable actuator progressively advance the toothed rack.

18. A plural fluid applicator according to claim 17 wherein the drive mechanism comprises first and second elongated links each having one and another end, the first link being pivotally secured at one end and having its other end hingedly coupled to one end of the second link the other end of the second link being coupled to said driving member, whereby operation of the actuator member causes said hinge to open, applying driving force along the links to the driving member.

19. An elongated manually actuated fluid sealant applicator suitable for dispensing a multicomponent biological sealant for surgical use, the applicator having an elongated body, being holdable in and operable by one hand of a user and comprising:
a) at least two cylindrical fluid reservoirs to contain, respectively, at least two fluid components of the biological sealant;
b) a movable actuator operable to dispense fluid from the applicator by displacement of fluid from the fluid containers;
c) at least two plungers, one for each reservoir, movable in the fluid reservoirs (30) to dispel fluid therefrom; and
c) a drive mechanism coupled with the plungers to translate the manually applied force on the movable actuator to a fluid displacing force exerted on each fluid in the fluid containers;

wherein the movable actuator is located intermediately of the length of the applicator and is movable transversely of the direction of movement of the plungers in the reservoirs and wherein the drive mechanism comprises a toothed rack coupled with the plungers for movement therewith and a slidably mounted reciprocal pawl engageable with the rack to advance the rack incrementally.

* * * * *